United States Patent [19]

Burdzy

[11] Patent Number: 5,518,728

[45] Date of Patent: May 21, 1996

[54] COSMETIC COMPOSITIONS FOR NON-WHITE PIGMENTED SKIN

[75] Inventor: Elisa Burdzy, Milford, N.J.

[73] Assignee: L'Oreal S.A., Paris, France

[21] Appl. No.: 287,268

[22] Filed: Aug. 8, 1994

[51] Int. Cl.⁶ .............................. A61K 7/00; A61K 7/021
[52] U.S. Cl. .............................. 424/401; 424/63; 514/844
[58] Field of Search ........................ 424/450, 401, 424/63; 514/844, 845

[56] References Cited

U.S. PATENT DOCUMENTS

| | | | |
|---|---|---|---|
| 4,137,302 | 1/1979 | Humbert et al. | 424/47 |
| 4,151,304 | 4/1979 | Evans | 424/361 |
| 4,379,136 | 4/1983 | Mochida | 424/65 |
| 4,425,327 | 1/1984 | Möller et al. | 424/65 |
| 4,481,186 | 11/1984 | Deckner | 424/59 |
| 4,537,782 | 8/1985 | Millet et al. | 514/774 |
| 4,622,074 | 11/1986 | Miyoshi et al. | 106/308 F |
| 4,664,909 | 5/1987 | Marschner | 424/65 |
| 4,863,800 | 9/1989 | Miyoshi et al. | 428/403 |
| 4,919,922 | 4/1990 | Miyoshi et al. | 424/63 |
| 4,980,167 | 12/1990 | Harashima et al. | 424/401 |
| 4,985,237 | 1/1991 | Matsuno et al. | 424/59 |
| 5,000,945 | 3/1991 | Kobayashi et al. | 424/59 |
| 5,023,075 | 6/1991 | Macchio | 424/63 |
| 5,073,364 | 12/1991 | Giezendanner et al. | 424/63 |
| 5,089,269 | 2/1992 | Noda et al. | 424/456 |
| 5,165,915 | 11/1992 | Tokubo et al. | 424/63 |
| 5,196,186 | 3/1993 | Omatsu et al. | 424/69 |
| 5,266,321 | 11/1993 | Shukazaki et al. | 424/401 |

FOREIGN PATENT DOCUMENTS 0140007  8/1983  Japan.
0228406  10/1985  Japan.

OTHER PUBLICATIONS

Product Description Sheet distributed by Westmin Talc, Amsterdam, The Netherlands (undated), Aug. 8, 1994.

*Primary Examiner*—Gollamudi S. Kishore
*Attorney, Agent, or Firm*—Brumbaugh, Graves Donohue & Raymond

[57] ABSTRACT

This invention relates to a cosmetic composition for non-white pigmented skin containing a surface treated talc having an average particle size about 60 μm, up to about 90 μm, preferably about 70 μm to about 90 μm. Such compositions cause no undesirable coloration, such as whiteness or greyness when applied to such skin.

11 Claims, No Drawings

COSMETIC COMPOSITIONS FOR NON-WHITE PIGMENTED SKIN

FIELD OF THE INVENTION

This invention relates to cosmetic compositions containing a surface treated talc of sufficient particle size that provides exceptional texture, transparency and enhanced function especially to non-white pigmented skin. The invention particularly relates to cosmetic compositions containing a talc having an average particle size about 60 µm, up to about 90 µm and is treated with a non-hydrogenated phospholipid material coated with a surface modifying agent.

BACKGROUND OF THE INVENTION

1. Technical Field

An area of continual research in the cosmetic product arts is the development of cosmetic compositions especially for non-white pigmented skin that afford to the user enhanced texture, transparency, moisturization, emolliency, and consistency. These features, however, are often abandoned in order to avoid undesirable coloration, such as "whiteness" or "greyness," when cosmetic compositions are applied to such skin. The term "non-white pigmented skin" refers to the tone of human skin, ranging from light yellow to dark brown. Non-white pigmented skin is commonly associated with, for example, Asians, Indians, American Indians, Hispanics and African Americans. Such skin is also associated with individuals whose skin has darkened from exposure to the sun, tanning machines or skin coloring agents. Typically, cosmetics containing either coated or uncoated talcs are opaque to non-white pigmented skin. Such talcs cause undesirable coloration, such as "whiteness" or "greyness," when applied to the surface of such skin. This is due to, inter alia, the limited particle size of these talcs. The average particle size of talc known and used in the art is about 2 µm to about 30 µm (by granulometer). Talcs having such a particle size range are unsuitable for cosmetic compositions for non-white pigmented skin because such talc prevents the natural tone of the skin to emerge freely through it, and consequently the tone of the skin appears unnatural. The term "undesirable coloration" refers to an unnatural appearance of the skin tone when compared to the natural tone of the user's skin. Further, it has been observed that cosmetic compositions currently available to individuals with non-white pigmented skin are scratchy and have an unpleasant effect when applied to the skin. This is due to the chemical agents added, as well as other modifications made, to these cosmetic compositions to eliminate undesirable coloration when cosmetic compositions are applied to non-white pigmented skin. It should be understood that, unless otherwise indicated, the average particle sizes of the talcs disclosed in the specification and the claims appended hereto are set forth in micrometers as measured by a granulometer.

2. Background Of The Prior Art

Undesirable coloration, such as "whiteness" or "greyness," commonly occurs on non-white pigmented skin when it is treated with cosmetic compositions containing talc. Attempts to rectify this problem have been made with little or no success, especially in dealing with skins of darker or richer tones. Such attempts included replacing talc with other components, such as mica, micronized polyethylene, and polymethylmethacrylate. However, it has been observed that these modified cosmetic compositions are inadequate in not only preventing undesirable coloration to the skin, but in skin adhesion and in skin feel. Further, these modified cosmetic compositions have a tendency to dry the skin and to feel coarse when applied.

Talc is one of the primary pigments used in cosmetic compositions. Pigments are those materials which form the base of the cosmetic composition and onto which coloring materials are introduced. Pigments establish the media by which the cosmetic composition is delivered.

However, since talc is exceedingly hydrophilic, it has been known in the art to treat the surface of talc with various agents to make the talc more water repellant (i.e. more hydrophobic) so that the talc will adhere to the skin, and yet repel moisture, thereby extending the wear duration of the talc.

A brochure listing the cosmetic products of Miyoshi Kasei Inc., distributed by U.S. Cosmetics Corp. (hereinafter "Miyoshi Brochure"), provides a comprehensive background on the use of surface treated talcs in the cosmetic industry. For many years, talc has been mixed with various oils and binders in cosmetic compositions. Typically, the talc in these cosmetic compositions was still too hydrophilic, and the resulting compositions would absorb sebum and flow with perspiration when applied to the surface of the skin. As the need to produce cosmetic compositions with greater hydrophobic properties became evident, metal soap was used. However, the surface properties of cosmetic compositions containing talc treated with metal soap were inconsistent, rough and uneven. Attempts to rectify these cosmetic compositions have been made using talc treated with, for example, silicones, amino acids, lecithins and hydrogenated lecithins. See e.g., Miyoshi Brochure; U.S. Pat. No. 4,622,074 (Miyoshi et al.); U.S. Pat. No. 4,863,800 (Miyoshi et al.); U.S. Pat. No. 4,919,922 (Miyoshi et al.); U.S. Pat. No. 5,073,364 (Miyoshi et al.); U.S. Pat. No. 5,073,364 (Giezendanner et al.).

Cosmetic compositions containing silicone treated talc sustain excellent water repellent characteristics and have been widely used in the cosmetic industry. There are, however, drawbacks in using talcs treated with silicone. Specifically, it has been observed that such talcs can be too hydrophobic and the surface of the talc becomes inactive. Skin adhesion and skin feel are often compromised, as silicone treated talcs have a tendency to be dry and coarse to the user's skin. Most significantly, known cosmetic compositions containing such talcs are not suitable for non-white pigmented skin, causing undesirable coloration when applied thereto, such as "whiteness" or "greyness."

Amino acid treated talcs provide "weak acidity" in the make-up powder products without losing water repellent properties. Such treated talcs also exhibit an improved moisturizing feeling in comparison to silicone treated talcs. Amino acid treatment turns the surface of talc weakly acidic, which approximates the pH of the skin and creates a much softer feeling to the user's skin. However, known cosmetics containing amino acid treated talcs are not suitable for non-white pigmented skin, causing undesirable coloration to the surface of such skin when applied thereto.

Lecithin is a glycerol-based phospholipid (similar to a triglyceride which does not contain phosphate), which naturally occurs in cell membranes. It has the general formula $CH_2OR_1$—$CH_2OR_2$—$CH_2OPO_2OHR_3$, where $R_1$ and $R_2$ are each fatty acids and $R_3$ is a small hydrophilic molecule selected from the group consisting of choline, ethanolamine, serine and inositol. Lecithin, which has a hydrophobic tail, comprising the two fatty acid chains ($R_1$ and $R_2$) and a hydrophilic head group comprising the phosphate group (—$PO_2O$—) and small hydrophilic molecule, possesses emulsifying, wetting and antioxidant properties. Lecithins may be extracted from organic sources such as egg yolk, soybean, corn and rapeseed oil, or may be synthetically prepared.

U.S. Pat. No. 5,073,364 of Giezendanner et al. teaches coating talc with lecithin in pressed powder cosmetics. It has been observed, however, that cosmetic compositions containing talc coated with lecithin generally develop an undesirable yellowish tinge over time. Such cosmetics also display a "draggy" and coarse texture, when applied to the user's skin.

Talcs treated with hydrogenated lecithin provide a smooth feeling to cosmetics and have better moisturizing effects than the amino acid treatments. However, cosmetic product wear is compromised due to the hydrophilic nature of the hydrogenated lecithin and its increased activity as a surfactant. Most significantly, as with known cosmetic compositions containing talc treated with lecithin, it has been observed that cosmetic compositions containing talc treated with hydrogenated lecithin can evidence color and odor change due to instability. Most significantly, it has been observed that known cosmetic compositions containing talc coated with either lecithin or hydrogenated lecithin are not suitable for non-white pigmented skin, causing undesirable coloration to the surface of such skin when applied thereto.

U.S. Pat. No. 4,622,074 of Miyoshi et al. teaches coating talc with a metal salt and a hydrogenated lecithin having an iodine value of less than 30 g/100 g. This iodine value was preferred so that problems with odor and color change can be avoided. See Col. 2, lines 30–34. The iodine value reflects the level of unsaturated fatty acids present in the lecithin used to coat the talc, with values for non-hydrogenated lecithins known to exceed 70 to 90 g/100 g. Cosmetic compositions containing talc coated with lecithin have a tendency to oxidize easily because the fatty acids ($R_1$ and $R_2$) in lecithin are mostly unsaturated and emit an unpleasant odor as a result of oxidation. Hydrogenation increases the level of fatty acid saturation in lecithin, up to 30 fold (See Miyoshi Brochure), thereby, as noted above, making it more stable as a useful coating agent for talc in cosmetic compositions.

U.S. Pat. No. 4,863,800 of Miyoshi et al. teaches coating talc with a saturated fatty acid triglyceride having an iodine value of not more than 5 g/100 g. U.S. Pat. No. 4,863,800 of Miyoshi et al. teaches coating of talc with polyolefin carrying—COOR groups (wherein R is hydrogen or metal).

It has been observed, however, that cosmetic compositions containing the coated talcs taught in the above-referenced U.S. patents to Miyoshi do not impart exceptional skin feel nor display an enhanced creamy texture. Most significantly, these cosmetic compositions are not suitable for non-white pigmented skin, causing undesirable coloration to the surface of such skin when applied thereto. This is due, inter alia, to the opacity of the talc, which has an average particle size of about 2 µm to about 7 µm. See Miyoshi Brochure.

Fatty acid esters are occasionally added to cosmetic compositions, typically for use as a surfactant (i.e., wetting agent and emulsifier). In U.S. Pat. No.5,196,186 (Omatsu et al.) and U.S. Pat. No. 5,165,915 (Tokubo et al.), examples of fatty acid esters commonly used for this purpose are provided. The fatty acid esters disclosed in Omatsu et al. and Tokubo et al., however, impart no emolliency, or any other desired attributes to non-white pigmented skin, such as translucency, to the disclosed compositions.

In view of the above, there is a need for a novel class of cosmetic compositions which provide not only beautifying effects to non-white pigmented skin, but also provide enhanced texture, translucency, moisturization, emolliency and consistency. Most significantly, there is also a need for a novel class of cosmetic compositions which afford the aforementioned qualities to non-white pigmented skin, without causing undesirable coloration, such as "whiteness" or "greyness."

SUMMARY OF THE INVENTION

It has now been found that a cosmetic composition for non-white pigmented skin of exceptional texture and enhanced function is provided by formulating a cosmetic composition containing a talc having an average particle size about 60 µm, up to about 90 µm, preferably about 70 µm to about 90 µm, and the surface of which is treated with a non-hydrogenated phospholipid material coated with a surface modifying agent. Most significantly, such a cosmetic composition causes no undesirable coloration, such as "whiteness" or "greyness," on the surface of non-white pigmented skin.

DETAILED DESCRIPTION OF THE INVENTION

The cosmetic composition of the present invention is provided by formulating a cosmetic composition containing a surface treated talc having a particle size about 60 µm, up to about 90 µm, and the surface of which is treated with a non-hydrogenated phospholipid material coated with a surface modifying agent. Preferably, the cosmetic composition of the present invention is provided by formulating a cosmetic composition containing a talc having an average particle size about 70 µm to about 90 µm and the surface of which is treated with a non-hydrogenated phospholipid material coated with a surface modifying agent selected from the group consisting of fatty acids, fatty acid esters or fatty acid triglycerides, silicones and mixtures thereof. The phospholipid material is preferably a lecithin from egg yolks, soy beans, corn or rapeseed, with soy bean lecithin being most preferred.

Talcs for use in the present cosmetic compositions may be obtained from Westmin Talc Inc. in Brighton, Mich., whose U.S. distributor is Ultra Chemical, Inc., Red Bank, N.J. Westmin Talc Inc. is a division of Western Mining Corp. of Australia. The production of such talcs, suitable for use in cosmetic compositions, is proprietary to Western Mining Corp., which is the assignee of U.S. patent application Ser. No. 08/141,953, filed 10/27/94, now pending, covering these talcs, their preparation and their use. However, the talcs disclosed in this application generally have an average particle size of 10 µm or less and are, thus, unsuitable for use in cosmetic compositions for non-white pigmented skin. Indeed, it has been observed that the small sized talc (10 µm or less) disclosed in this application is in fact inappropriate for cosmetic compositions for use on non-white pigmented skin, causing undesirable coloration to the skin, such as "whiteness" or "greyness", when applied thereto.

A significant attribute of the cosmetic compositions is the range of particle distribution of the talc component, which affords cosmetic compositions made with the talc having an exceedingly transparent surface. The average particle size of the talc in the present cosmetic composition can range from about 60 µm, up to about 90 µm. Preferably the average particle size range of the talc is about 70 µm to about 90 µm. This unusual distribution of large particle size is unique to the talc used in the present cosmetic composition and is unknown in any other talc in the art, which provide far less transparency. Known talcs generally have an average particle size range of about 2 μm to about 30 μm. It has been observed that known cosmetic compositions containing talc of this smaller particle size cause undesirable coloration to non-white pigmented skin when applied thereto. It was therefore recognized that the present talc in a cosmetic composition would provide a significant transparency that would allow the natural tone of non-white pigmented skin to emerge free from undesirable coloration, such as "whiteness" or "greyness," when such a composition is applied thereto. Indeed, cosmetic compositions preferably containing the present talc having an average particle size about 70 μm to about 90 μm do in fact cause no undesirable coloration, such as "whiteness" or "greyness," when applied to the surface of non-white pigmented skin. Such cosmetic compositions are therefore particularly suited to the development of cosmetic products for individuals having such skin.

Further, in comparing cosmetic compositions containing known talcs used in the cosmetic industry, including, for example, talcs treated with lecithin, hydrogenated lecithin, amino acids, metal soaps and combinations of hydrogenated lecithin and metal soap, with the present cosmetic compositions comprising talc having an average particle size about 70 μm to about 90 μm and treated with a non-hydrogenated phospholipid material coated by a surface modifying agent, it was recognized that the attributes of the claimed cosmetic composition imparted by the present coated talc were far superior over the other talcs used in the cosmetic industry. These attributes include, for example, enhanced texture, high slip characteristics and exceptional creamy texture. It was therefore recognized that talc having an average particle size about 60 μm, up to about 90 μm and treated with a non-hydrogenated phospholipid material coated with a fatty acid ester would allow for the development of a novel class of improved cosmetic compositions for individuals with non-white pigmented skin, including but not limited to, powder foundations, oil free makeups, two way cake foundations, mascaras, emulsions (including makeup and moisturizers), lipsticks, eye liners, cream blushes, rouges and creme makeups.

These and other embodiments of the invention will be made readily apparent to those of ordinary skill in the cosmetic composition arts in view of the disclosure herein. Further, the practice of the present invention employs, unless otherwise indicated, conventional techniques known to those of ordinary skill in the cosmetic composition art.

As noted, cosmetic compositions for non-white pigmented skin are available to the cosmetic industry. But these compositions are generally inferior products as discussed. Prior to the present invention, superior cosmetic compositions containing a surface treated talc, having an average particle size about 60 μm, up to about 90 μm, which provide the improved characteristics for non-white pigmented skin previously described, have not been available. Further, the texture, transparency and particle distribution of cosmetic compositions containing talc having a particle distribution of large-sized particles, and the surface of which is treated with a non-hydrogenated phospholipid coated with a surface modifying agent, exceed that of any other cosmetic composition developed for non-white pigmented skin. Uncoated talc of the disclosed size range, about 60 μm to about 90 μm, preferably about 70 μm to about 90 μm, possesses a truly unique, nearly micaceous quality. With the addition of the phospholipid material coated with a surface modifying agent, such as a fatty acid ester, the attributes of the uncoated talc are greatly enhanced.

The present cosmetic compositions preferably comprise surface treated talc having an average particle size about 60 μm, up to about 90 μm, more preferably about 70 μm to about 90 μm. The surface of such talc is treated with a non-hydrogenated phospholipid material, preferably lecithin, which is coated with a surface modifying agent selected from the group consisting of fatty acid esters or fatty acid triglycerides, silicones and mixtures thereof, preferably a fatty acid ester.

The talc treated with a non-hydrogenated phospholipid which is coated with the above-mentioned groups of surface modifying agents may be present in the cosmetic composition in any suitable amounts. For example, such talc may be present in amounts of from approximately 10 to 70% by weight. Preferably the talc is present in amounts of from approximately 20 to 60% by weight.

The non-hydrogenated phospholipid material on the present talc may be of any suitable type. A lecithin material is preferred, where the lecithin most preferably has a high phospholipid content. Lecithin containing phosphatidylcholine, phosphatidylethanolamine, phsophatidylinositol, phosphatidylserine or mixtures thereof may be used. The lecithin may be obtained from a natural source or synthetically produced. A lecithin material purified from naturally occurring lecithin found in any suitable vegetable matter, for example soybean, egg, corn or rapeseed may be used. In general, the lecithin material may be or at least substantially comprise commercially available lecithin of various grades suitable for use in a cosmetic composition. The lecithin also may be or at least substantially comprise the specific compound identified as lecithin.

Such non-hydrogenated lecithins may comprise phosphatidylcholine as the sole phosphate containing hydrophilic molecule, or they can contain other phosphate containing molecules, such as phosphatidylethanolamine, phosphatidylserine and phosphatidylinositol. The non-hydrogenated lecithins may also comprise neutral fat from egg yolk, soybean, corn or rapeseed. As used herein, the term "lecithin" refers to the overall phospholipid composition, which may contain neutral fat as well. A preferred non-hydrogenated lecithin for use in the present cosmetic compositions is soybean lecithin, having an iodine value of about 87 g/100 g and a phospholipid content of about 75% and a fatty acid content of about 25%.

It has surprisingly been found that non-hydrogenated lecithin may be used in the present cosmetic compositions. Contrary to what is known in the art, it is unnecessary to hydrogenate the lecithin to avoid the development of unpleasant odor. Also the emulsifying activity of the lecithin provides a suitable carrier for other compounds, including other phospholipids, and makes them more available to the skin than does a hydrophobic material.

The non-hydrogenated phospholipid material may be present in any suitable amounts. The non-hydrogenated phospholipid material may be present in an amount of from approximately 0.5 to 3% by weight, based on the total weight of the surface treated talc in the cosmetic composition, preferably approximately 1 to 2% by weight, more preferably approximately 1.50% by weight.

Accordingly, in a preferred embodiment of the present invention there is provided a cosmetic composition comprising a surface treated talc having an average particle size about 60 μm, up to about 90 μm, more preferably about 70 μm to about 90 μm. Such surface-treated talc comprises approximately 10 to 70% by weight of the cosmetic composition. The non-hydrogenated phospholipid material comprises approximately 0.5 to 3% by weight, based on the weight of the surface treated talc in the cosmetic composition. The non-hydrogenated phospholipid material, preferably lecithin, is coated with a surface modifying agent which may include fatty acids, fatty acid esters or triglycerides, all suitable and cosmetically approved silicones, dimethicones, cyclomethicones, teflon, and mixtures thereof, preferably a fatty acid ester.

The surface modifying agent which can be used to coat the non-hydrogenated phospholipids on the talc surface may include fatty acids such as oleic, palmitic, stearic, linoleic, linolenic acid or mixtures thereof. The fatty acid esters may include isocetyl stearate, diisopropyl dimerate, neopentanoate, isocetylstearyl stearate, isopropyl isostearate, diisostearyl dilinoleate, diisostearyl dilinoleate octadecyl palmitate, isocetyl stearoyl stearate, octyl palmitate, isostearyl isostearate, micro crystalline triglyceride and mixtures thereof. Preferred fatty acid esters include isocetyl stearoyl stearate and diisopropyl dimerate.

Triglycerides may include, caprylic acid, caprylic/capric triglycerides, caprylic/capic linoleic acid, dicaprylate, dicaprate, hydrogenated palm oil, hydrogenated coconut oil, glyceryl stearate, cocoglycerides or hydrogenated soybean oil.

Silicones may include dimethicone, simethicone, cyclomethicone and mixtures thereof. The silicone component may be provided in the form of a liquid, wax or gum.

The surface modifying agent may include a fatty acid ester component, optionally together with a fatty acid, triglyceride or silicone component, vitamins such as vitamin E or A, all amino acids such as lauroyl lysine, leucine or any suitable amino acid for treatment of the skin.

The cosmetic compositions of the present invention can vary, with the selection of surface modifying agent or mixture thereof, in transparency, texture, hydrophilicity, binding capability, emulsifying capability, oil absorption, treatment to the skin, etc. The resulting compositions are quite stable, have good ageing characteristics, and little odor. Depending upon the surface modifying agent used, the stability of the compositions are equal to or better than products produced from using hydrogenated lecithins.

The surface modifying agent may be present in any suitable effective amounts. The surface modifying agent may be present in amounts of from approximately 0.05 to 0.5% by weight, based on the total weight of the surface treated talc in the cosmetic composition, preferably approximately 0.25% by weight.

A preferred surface treated talc can comprise the following components:

TABLE 1

| Ingredient | % by weight |
| --- | --- |
| talc ($Mg_3Si_4O_{10}(OH)_2$) | ~98.00% |
| lecithin (non-hydrogenated) | ~1.50% |
| fatty acid ester | ~0.25% |
| mineral contaminants | ~0.25% |

The average particle size of the coated talc used in the present invention may vary according to the intended skin tone for which the cosmetic composition is made. Based on such skin tone, determination of an effective particle size can be made without undue experimentation by those of ordinary skill in the cosmetic art. The average particle size of the present talc is about 60 μm, up to about 90 μm, with the preferred average size in cosmetic compositions for non-white pigmented skin being about 70 μm to about 90 μm.

It should be noted that the specifically disclosed amounts of surface modifying agents used to coat the non-hydrogenated phospholipid are exemplary in nature and are not to be construed as limiting the scope of the invention as set forth in the appended claims. For example, the amount of modifying agents which can be used to coat the non-hydrogenated phospholipid used to treat the surface of the talc in the cosmetic composition of the present invention may vary according to the specific features of that cosmetic composition. Such features include, for example, the media by which the cosmetic composition is applied to the skin, the shade of the cosmetic composition and the intended wear duration of the cosmetic composition. Each such feature governs the level of hydrophobicity for that cosmetic composition. Accordingly, the hydrophobicity of the cosmetic composition of the present invention can be adjusted according to these features, for example, by changing the ratio of non-hydrogenated phospholipid to modifying surface agents on the coated talc. For example, a higher fatty acid ester :lecithin ratio will render the talc less hydrophobic.

It should be noted that the specifically disclosed amounts of the present coated non-hydrogenated phospholipid used to treat the surface of the talc in the present cosmetic composition are exemplary in nature and not to be construed as limiting the scope of the invention as set forth in the appended claims. For example, the amount of the present coated non-hydrogenated phospholipid on such talc may vary according to the intended purpose for which the cosmetic composition is made. Based on such purpose, determination of an effective coating onto the present talc can be made without undue experimentation by those of ordinary skill in the cosmetic art. A preferred weight percent of a lecithin coated with fatty acid ester which can be added to the talc of the present invention is about 1.75 (i.e about 1.50% lecithin and about 0.25% fatty acid ester).

The following examples, which are not intended to limit the scope of the present invention, illustrate the preparation of cosmetic compositions comprising the talc described in Table 1.

EXAMPLE 1

The following ingredients were used to form an oil-free two way cake foundation containing the talc described in Table 1.

| An Oil-Free Two Way Cake Foundation | |
| --- | --- |
| Ingredient | % by weight |
| PHASE A | |
| Talc of Table 1 with an average particle size about 70 μm to 90 μm (by granulometer) | 44.65 |
| Mica | 20.00 |
| Zinc Palmitate | 5.00 |
| Kaolin | 5.00 |
| Silica | 5.00 |
| Nylon-12 | 3.00 |
| Isopropyl Titanium Trisostearate | 0.25 |
| Boron Nitride | 0.30 |
| Lauroyl Lysine | 0.10 |
| Acrylates Copolymer | 0.05 |
| Preservatives | 0.50 |
| Pigments | 8.50 |
| PHASE B | |
| Dimethicone | 5.50 |
| Cetyl Dimethicone | 0.90 |
| Trisocetyl Citrate | 0.75 |

An Oil-Free Two Way Cake Foundation

| Ingredient | % by weight |
| --- | --- |
| Trimethyl Siloxysilicate | 0.50 |

Phase A was combined and fluidized via a Hockmeyer mixer and then micronized. The micronized mixture was returned to the mixing vessel. Phase B was combined and sprayed into Phase A via injection tank. Phase A and B were fluidized and then micronized. The bulk was pressed into metal godets.

The resulting product was applied to the surface of human skin with a dry puff or a sponge dampened with water and observed for effect and performance. The resulting product was found to be superior in emolliency, in pick-up onto the sponge, in adhesion to the skin, in comfort on the skin, in appearance on the skin and in overall wear. Most significantly, no undesirable coloration such as "whiteness," "greyness" or opacity was evident on the surface of non-white pigmented skin. The resulting product was found to enhance the beauty of such skin and maintain its true color.

The product as described in this example is a significant improvement upon another known cosmetic composition which contains talc coated with lecithin. It is available to the cosmetic industry and is known as Lancome DUAL FINISH® Versatile Powder Makeup, distributed in the United States by Cosmair, Inc. This product, however, has several limitations when compared to the cosmetic composition of the present invention. For example, the limited average particle size of the talc (about 10 µm to about 30 µm) makes it unsuitable for the development of multiple shades for non-white pigmented skin. Attempts to make such shades using talc coated with this lecithin resulted in cosmetic compositions which caused undesirable "whiteness," "greyness" or opacity when applied to the surface of non-white pigmented skin. Further, the resulting cosmetic compositions tended to exhibit an unnatural green tone, making it unappealing to consumers.

It has been observed that the overall performance of the cosmetic composition described in this example is significantly improved upon direct comparison to the former product utilizing talc having an average particle size of about 10 µm to about 30 µm and coated with lecithin only. Such improvements include, for example, exceptional resistance to glazing after repeated usage, a softer creamier feeling when applied to the skin and enhanced ability for both wet and dry applications.

EXAMPLE 2

The following ingredients were used to form a two-way cake foundation containing the talc described in Table 1.

A Two-Way Cake Foundation

| Ingredient | % by weight |
| --- | --- |
| PHASE A | |
| Talc of Table 1 with an average particle size of about 70 µm to about 90 µm (by granulometer) | 41.85 |
| Magnesium Myristrate | 0.50 |
| Zinc Palmitrate | 1.00 |
| Mica | 30.00 |
| Nylon-12 | 1.25 |
| Kaolin | 5.00 |
| Preservatives | 0.90 |
| Pigments | 8.50 |
| PHASE B | |
| Octyl Dodecyl Stearoyl Stearate | 1.00 |
| Maleated Soybean Oil | 6.25 |
| Dioctyl Maleate | 1.00 |
| Phenyl Trimethicone | 2.75 |

Phase A was combined and fluidized via a Hockmeyer mixer and then micronized. The micronized mixture was returned to the mixing vessel. Phase B was combined and sprayed into Phase A via injection tank. Phase A and B were fluidized and then micronized. The bulk was pressed into metal godets.

The resulting product was applied to the surface of human skin and observed for effect and performance. The resulting product was found to be superior in emolliency, in pick-up onto the sponge, in adhesion to the skin, in comfort on the skin, in appearance on the skin and in overall wear. Most significantly, no undesirable "whiteness," "greyness" or opacity was evident on the surface of non-white pigmented skin. The resulting product was found to enhance the beauty of such skin and maintain its true color.

Surprisingly, the unsaturated fatty acid content of the non-hydrogenated lecithin of the surface treated talc used in examples 1 and 2 is quite high, having an iodine value greater than 30 g/100 g and preferably about 87 g/100 g. Unlike other lecithin-coated talcs having a comparable iodine value (and contrary to the teachings of Miyoshi, e.g., U.S. Pat. No. 4,622,074 at Col. 2, lines 30–34), the present talc treated with a phospholipid coated with a fatty acid ester is stable. Cosmetic compositions containing this talc exhibit no problem of color and odor change. In addition, unlike the cosmetic compositions currently available, it has been observed that cosmetic compositions containing this talc can be applied to non-white pigmented skin without causing undesirable coloring, such as "whiteness" or "greyness." This attribute is due mainly to (1) the range of large size particles of the talc used in the present cosmetic composition, including particles of up to about 90 µm; and (2) the treatment of the talc with a non-hydrogenated phospholipid coated with a surface modifying agent. Further, it has been observed that the surface qualities and skin feel of cosmetic compositions containing the surface treated talcs used in examples 1 and 2 are far greater than those cosmetic compositions currently available for non-white pigmented skin.

The invention illustratively disclosed herein suitable may be practiced in the absence of any element which is not specifically disclosed herein.

Further, it should be understood that the specifically disclosed embodiments are exemplary in nature and not to be construed as limiting the scope of the invention, as set forth in the appended claims. For example, the cosmetic composition of the present invention may be in any form, including but not limited to, powder products, mascaras, emulsions (including make-up and moisturizers), lipsticks, eye liners, lip liners, creme blushes and creme makeups. Additionally, the amounts of ingredients described in each embodiment can be adjusted according to the specific features of the cosmetic composition into which the talc of the present invention is incorporated by those skilled in the cosmetic composition art without undue experimentation.

I claim:

1. A cosmetic composition for non-white pigmented skin comprising a surface treated talc having an average particle size of about 60 μm, up to about 90 μm, wherein the talc has a double coating thereon, wherein a first coat comprises a non-hydrogenated phospholipid having an iodine value of greater than about 30 g/100 g and a second coat comprises a surface modifying agent, wherein the surface modifying agent is a fatty acid ester.

2. The cosmetic composition of claim 1, wherein the surface treated talc comprises 0.5 to 3% by weight of the non-hydrogenated phospholipid.

3. The cosmetic composition of claim 1, wherein the non-hydrogenated phospholipid is a lecithin.

4. The cosmetic composition of claim 3, wherein the lecithin is soybean lecithin.

5. The cosmetic composition of claim 3, wherein the iodine value of the lecithin is about 87 g/100 g.

6. The cosmetic composition of claim 3, wherein the lecithin comprises about 25 weight percent fatty acid and about 75 weight percent phospholipid.

7. The cosmetic composition of claim 1, wherein the fatty acid ester is isocetyl stearoyl stearate.

8. The cosmetic composition of claim 1, wherein the fatty acid ester is diisopropyl dimerate.

9. The cosmetic composition of claim 1, wherein the surface treated talc comprises about 1.5 weight percent non-hydrogenated phospholipid and about 0.25 weight percent surface modifying agent based on the weight of said talc in the cosmetic composition.

10. The cosmetic composition of claim 1, wherein the surface treated talc comprises 0.05 to 0.5% by weight of the surface modifying agent.

11. A cosmetic composition for non-white pigmented skin consisting essentially of a surface treated talc having an average particle size of about 60 μm, up to about 90 μm, wherein the talc has a double coating thereon, wherein a first coat comprises a non-hydrogenated phospholipid having an iodine value of greater than about 30 g/100 g and a second coat comprises a surface modifying agent selected from the group consisting of fatty acid esters, silicone and mixtures thereof.

* * * * *